(12) United States Patent
Hoekzema

(10) Patent No.: US 12,175,967 B2
(45) Date of Patent: Dec. 24, 2024

(54) TOUCH-FREE, VOICE-ASSISTANT, AND/OR TRACKING SYSTEMS AND METHODS FOR AUTOMATING INVENTORY GENERATION AND TRACKING OF CHILDCARE PRODUCTS

(71) Applicant: The Procter & Gamble Company, Cincinnati, OH (US)

(72) Inventor: Brad S. Hoekzema, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 294 days.

(21) Appl. No.: 17/514,027

(22) Filed: Oct. 29, 2021

(65) Prior Publication Data

US 2022/0139378 A1    May 5, 2022

Related U.S. Application Data

(60) Provisional application No. 63/107,775, filed on Oct. 30, 2020.

(51) Int. Cl.
 *G06F 17/00* (2019.01)
 *A61F 13/42* (2006.01)
 (Continued)

(52) U.S. Cl.
 CPC .............. *G10L 15/08* (2013.01); *A61F 13/42* (2013.01); *A61F 13/84* (2013.01);
 (Continued)

(58) Field of Classification Search
 CPC .... G10L 15/08; G10L 2015/088; A61F 13/42; A61F 13/84; A61F 2013/424; A61F 2013/8479
 (Continued)

(56) References Cited

U.S. PATENT DOCUMENTS 7,699,222 B2    4/2010  Uchitani
2001/0037220 A1   11/2001  Merry
 (Continued)

FOREIGN PATENT DOCUMENTS

WO    2018152410    8/2018

OTHER PUBLICATIONS

AttendanceBot and sub-modules thereof; available at least 6_20 from archive.org (Year: 2020).*
 (Continued)

*Primary Examiner* — Paul C McCord
(74) *Attorney, Agent, or Firm* — Daniel S. Albrecht (57) ABSTRACT

Touch-free, voice-assistant, and/or tracking systems and methods are described for automating inventory generation and tracking of childcare products. In various aspects, the touch-free, voice-assistant, and/or tracking systems and methods comprise receiving, by one or more processors, one or more name values corresponding to one or more children of a childcare program associated with at least one physical childcare location. A childcare product inventory, comprising a childcare product of at least one product type, is generated based on a count of the one or more name values. Child event data is received comprising information related to use of the childcare product. The child event data is based on audible input of a user as received via a voice command interface of a voice-assistant application (app) as implemented on a voice assistance device. The childcare product inventory may be updated based on the child event data.

21 Claims, 6 Drawing Sheets

(51) Int. Cl.
*A61F 13/84* (2006.01)
*G10L 15/08* (2006.01)

(52) U.S. Cl.
CPC . *A61F 2013/424* (2013.01); *A61F 2013/8479* (2013.01); *G10L 2015/088* (2013.01)

(58) Field of Classification Search
USPC ........................................................ 704/200
See application file for complete search history.

(56) References Cited

U.S. PATENT DOCUMENTS

| | | | |
|---|---|---|---|
| 2017/0116643 A1* | 4/2017 | Berg | G06Q 30/0623 |
| 2017/0308826 A1* | 10/2017 | Fewster | G06Q 10/0631 |
| 2018/0047297 A1 | 2/2018 | Harper-ray | |
| 2018/0325469 A1 | 11/2018 | Fountaine | |
| 2019/0326015 A1 | 10/2019 | Cannell | |
| 2022/0180861 A1 | 6/2022 | Hoekzema | |

OTHER PUBLICATIONS

Non Final Office Action; U.S. Appl. No. 17/678,095 dated Nov. 9, 2023.

\* cited by examiner

| | | |
|---|---|---|
| 302 | 00:00 | Hey Alexa, Open Smart daycare staging. |
| | 00:05 | Hello and happy Tuesday. Who will you be changing today? Make |
| | 00:08 | sure you tell me the type of change in the size. |
| | 00:13 | Jackson size 3 wet. |
| | 00:17 | So you're changing Jackson with a size 3 diaper for a wet change. |
| | 00:21 | Is that right? Yes. |
| | 00:27 | Thanks so much for that. Enjoy your day. |
| 304 | 00:31 | Hey Alexa, Open Smart daycare staging. |
| | 00:36 | Good afternoon excited for another great Tuesday, who's |
| | 00:39 | getting changed make sure you also tell me the size and the |
| | 00:43 | type of change. |
| | 00:45 | Sophia size 2 BM. |
| | 00:50 | Was that Sophia Rainer or Sophia McMahon? |
| | 00:54 | Sofia Rainer |
| | 00:57 | so you're changing Sophia with a size 2 diaper for a BM. Change. |
| | 01:02 | Is that right, yes. |
| | 01:07 | Thank you, I've just recorded that change. Enjoy your day. |
| 306 | 01:12 | Hey Alexa, Open Smart daycare staging. |
| | 01:17 | Aja and happy Tuesday. Who are you changing now? Make sure you |
| | 01:20 | tell me the type of change in |
| | 01:23 | the size. Lucas size for dry. |
| | 01:28 | So you're changing Lucas with a size 4 diaper for a dry change, |
| | 01:32 | is that right? The name is wrong. |
| | 01:36 | What name should it be instead Emily? |
| | 01:41 | So you're changing Emily with a size 4 diaper for a dry change. |
| | 01:46 | Is that right? Yes. |
| | 01:51 | Thank you, I've just recorded that change. Enjoy your day. |

TOUCH-FREE, VOICE-ASSISTANT, AND/OR TRACKING SYSTEMS AND METHODS FOR AUTOMATING INVENTORY GENERATION AND TRACKING OF CHILDCARE PRODUCTS

CROSS REFERENCE TO RELATED APPLICATION

This application claims the benefit of U.S. Provisional Application No. 63/107,775, filed Oct. 30, 2020, the substance of which is incorporated herein by reference.

FIELD OF THE DISCLOSURE

The present disclosure generally relates to touch-free, voice-assistant, and/or tracking systems and methods, and, more particularly, to touch-free, voice-assistant, and/or tracking systems and methods for automatic inventory generation and tracking of childcare products.

BACKGROUND

Typically, handling of childcare products by a company or institution, involves regulatory and/or other legal hurdles related to health and safety of children. This can involve monitoring and/or management of childcare products to ensure legal compliance. Conventional methods of tracking and management of such childcare products includes manual handling and inventory allocation, typically performed by school administrators of a given childcare related program. For example, for diaper related products, such management typically includes manual recording of each diaper change (as required by law), which takes time and effort by program participants.

In addition, teachers and/or other administrators of childcare related programs must typically touch or handle the childcare products (e.g., diapers). For example, conventional techniques typically require the teacher and/or other administrator to perform data entry, e.g., by touching or handling a keyboard to record their interaction or use of such childcare products. Such manual handling typically occurs after the teacher and/or other administrator has handled a childcare product (e.g., a diaper). This activity can lead to unsanitary conditions. Such practice is particularly egregious during more recent times, involving the novel Coronavirus Disease (COVID-19), and other related infectious diseases.

Similarly, in some cases, parents of the children may need to provide the teacher and/or other administrator with the childcare products, which can increase activity, transfer, and possibly introduce transfer of disease among the participants of the childcare related program.

In addition, allocation and management of the childcare products, as allocated or used on a per child basis, is difficult, especially for sizable childcare related programs involving many participants, e.g., children, parents, teachers, administrators, etc.

For the foregoing reasons, there is a need for touch-free, voice-assistant, and/or tracking systems and methods for automatic inventory generation and tracking of childcare products.

BRIEF SUMMARY

As described for various embodiments herein, touch-free and voice-assistant systems and methods are described for automatic inventory generation and tracking of childcare products. Such systems and methods provide several benefits. For example, touch-free and voice-assistant systems and methods provide a voice app and related voice command interface that may be configured to integrate with existing software platforms (e.g., school software platforms) such that teachers and/or school administrators do not have to manually touch, handle, and/or enter childcare product information, which can reduce possible disease transmission, especially among multiple devices, and therefore improve overall health and safety. It should be understood that inventive systems of the present disclosure may be touch-free and voice-assistant systems, but inventive embodiments may also be voice-assistant systems that are not touch-free. For example, a voice-assistant system of the present disclosure may be both voice controlled (or voice interactive) and touch controlled (or touch interactive). Further, systems of the present disclosure may require a user, in some instances, to use voice commands, and in other instances, require the user to use touch commands. Still further, systems of the present disclosure may require a user, in some instances, to use voice commands, and in other instances, give the user an option to use voice commands or touch commands. Systems of the present disclosure may allow the user, in all instances, to optionally use voice or touch commands. And, in yet other embodiments, systems of the present disclosure may require a user in all instances to use voice commands, providing no option for a touch command.

In addition, a voice app and related voice command interface, as described herein, may provide a streamlined and more efficient use, for both an underlying computing system and its users, via simplification of voice commands. For example, touch-free and voice-assistant systems and methods, as described herein, allow a user to record usage of a childcare product (e.g., diaper change activity) via a voice command. For example, such voice commands can represent a small portion of child event data (e.g., "Johnny, Size 3, Wet" for diaper related childcare products) that is efficiently parse-able by a processor and storable on a database or other storage device. Such activity is automatically stored to the child's account, saving effort, time, and possible contamination from an otherwise need for manual data entry, e.g., via a keyboard or a computer tablet app. Such voice command implementation also provides a convenient and efficient delivery system, which enables parents and operators to focus on children in a disease-safe and healthy environment, which promotes the health of children, parents, teachers, administrators, and the like. In addition, such voice command implementation eliminates the need for school administrators to monitor childcare products (e.g., diapers and/or wipes) inventory, and allows for tracking and/or reporting of inventory for continuous automatic management, maintenance, and otherwise as describe herein.

More specifically, as described herein for various embodiments, a touch-free and voice-assistant system is disclosed. The touch-free and voice-assistant system may be configured to automate inventory generation and tracking of childcare products. The touch-free and voice-assisted system may comprise a voice-assistant application (app) including computing instructions configured for implementation on a voice assistant device. The voice-assistant app may further comprise a voice command interface configured to receive an audible input of a user. The touch-free and voice-assistant system may further comprise a server comprising one or more processors and one or more memories. The server may be communicatively coupled via a computer network to the voice-assistant app. The server may comprise computing instructions configured to execute on the one or more processors of the server, wherein the computing instructions, when executed by the one or more processors, cause the one or more processors of the server to receive one or more name values corresponding to one or more children of a childcare program associated with at least one physical childcare location. The computing instructions, when executed by the one or more processors, may further cause the one or more processors of the server to generate a childcare product inventory based on a count of the one or more name values. The childcare product inventory may comprise a childcare product of at least one product type. The computing instructions, when executed by the one or more processors, may further cause the one or more processors of the server to receive child event data, from the voice-assistant app, comprising information related to use of the childcare product. The child event data may be based on the audible input of the user. The computing instructions, when executed by the one or more processors, may further cause the one or more processors of the server to update the childcare product inventory based on the child event data.

In addition, as described herein for various embodiments, a touch-free and voice-assistant method for automating inventory generation and tracking of childcare products is disclosed. The touch-free and voice-assisted method may comprise receiving, by one or more processors, one or more name values corresponding to one or more children of a childcare program associated with at least one physical childcare location. The touch-free and voice-assisted method may further comprise generating, by the one or more processors, a childcare product inventory based on a count of the one or more name values. The childcare product inventory may further comprise a childcare product of at least one product type. The touch-free and voice-assisted method may further comprise receiving, by the one or more processors, child event data comprising information related to use of the childcare product. The child event data may be based on audible input of a user as received via a voice command interface of a voice-assistant application (app) as implemented on a voice assistance device. The touch-free and voice-assisted method may further comprise updating, by the one or more processors, the childcare product inventory based on the child event data.

Still further, in various embodiments, a tangible, non-transitory computer-readable medium storing instructions for automating inventory generation and tracking of childcare products is disclosed. The instructions, when executed by one or more processors, may cause the one or more processors to receive one or more name values corresponding to one or more children of a childcare program associated with at least one physical childcare location. The instructions, when executed by one or more processors, may further cause the one or more processors to generate a childcare product inventory based on a count of the one or more name values. The childcare product inventory may comprise a childcare product of at least one product type. The instructions, when executed by one or more processors, may further cause the one or more processors to receive child event data comprising information related to use of the childcare product. The child event data may be based on audible input of a user as received via a voice command interface of a voice-assistant application (app) as implemented on a voice assistance device. The instructions, when executed by one or more processors, may further cause the one or more processors to update the childcare product inventory based on the child event data.

In accordance with the above, and with the disclosure herein, the present disclosure includes improvements in computer functionality or in improvements to other technologies at least because the disclosure recites that, e.g., a voice command interface is implemented on a touch-free and voice-assisted system where the voice command interface, in various embodiments, is used to control, via audible input, the system. That is, the present disclosure describes improvements in the functioning of the computer itself or "any other technology or technical field" because the voice command interface allows audible input that reduces the processing and/or memory requirements compared to a traditional text interface. This improves over the prior art at least because the voice command interface alleviates memory and/or processing resources of the underlying system (e.g., processors of a server or otherwise), where such processing, at least in some embodiments, can be offloaded to a voice assistant device that processes succinct data (e.g., child event data) and that spreads processing across a voice assistant device and an underlying server. Such processing, across differently configured devices, configured for specific processing, reduces processing resources as required by the system as a whole, and allows the system to operate more efficiently.

In addition, the present disclosure includes applying certain features with, or by use of, a particular machine, e.g., a voice assistant device used to receive an audible input of a user, and process the audible input of the user to determine specific information, e.g., child event data as described herein.

Furthermore, the present disclosure includes effecting a transformation or reduction of a particular article to a different state or thing, e.g., an audible input of a user is transformed or reduced to a command for automatic inventory generation and tracking of real-world childcare products.

Still further, the present disclosure includes specific features other than what is well-understood, routine, conventional activity in the field, or adding unconventional steps that confine the claim to a particular useful application, e.g., touch-free and voice-assistant systems and methods configured to automate inventory generation and tracking of childcare products.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

The Figures depict preferred embodiments for purposes of illustration only. Alternative embodiments of the systems and methods illustrated herein may be employed without departing from the principles of the invention described herein.

DETAILED DESCRIPTION

Figure 1A:
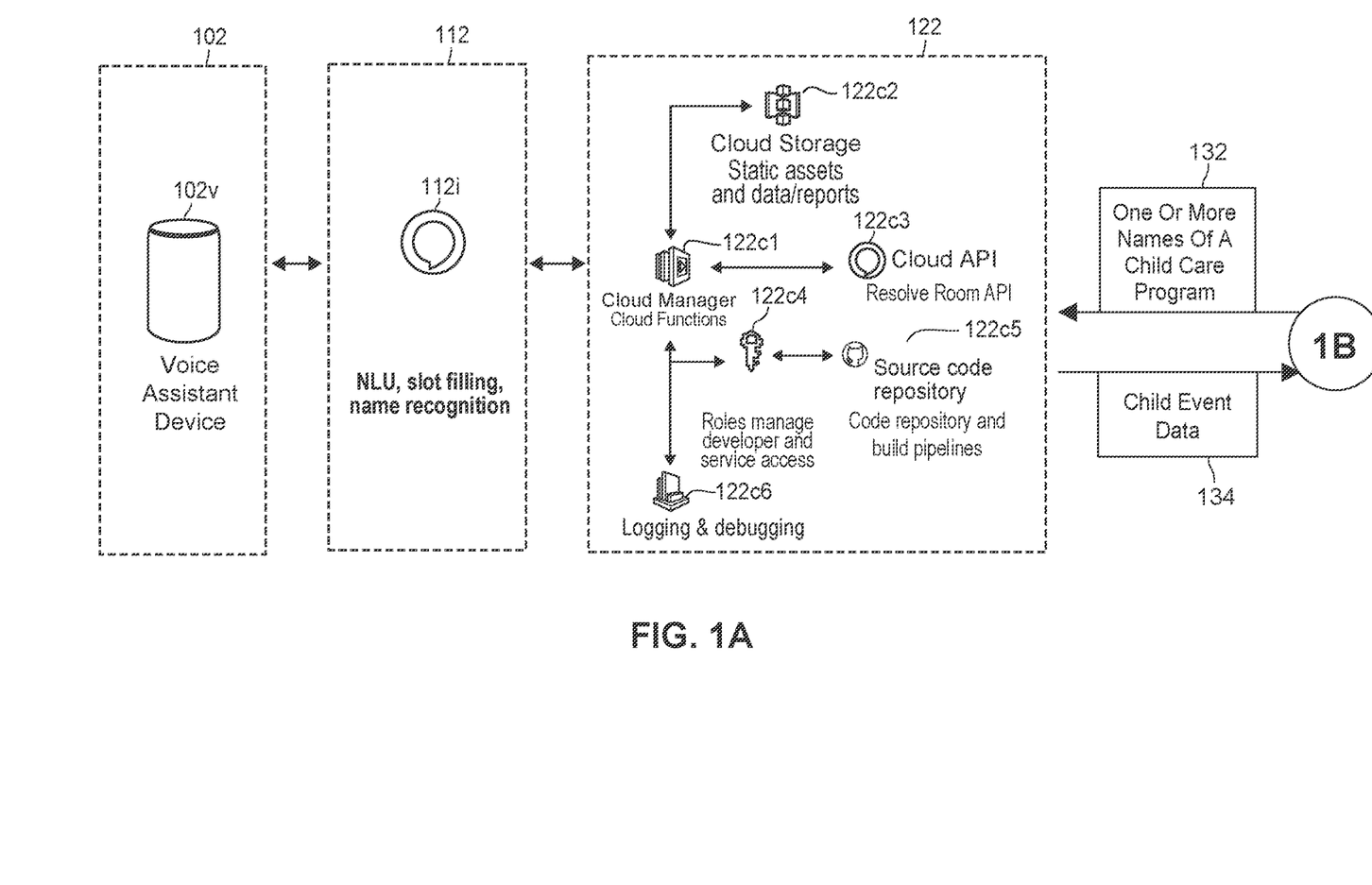
FIG. 1A illustrates an example touch-free and voice-assistant system in accordance with various embodiments disclosed herein.

FIG. 1A illustrates an example touch-free and voice-assistant system 100 in accordance with various embodiments disclosed herein. In the example of FIG. 1, touch-free and voice-assistant system 100 includes a voice-assistant application (app) comprising computing instructions configured for implementation on a voice assistant device 102v. In various embodiments, voice assistant device 102v may comprise a home assistant device and/or personal assistant device, including, by way of non-limiting example, any one or more of a GOOGLE HOME device, an AMAZON ALEXA device, an ECHO SHOW device, or the like. In addition, voice assistant device 102v may also be or comprise a cellular phone, a mobile phone, a tablet device, a personal data assistance (PDA), or the like, including, by non-limiting example, an APPLE iPhone or iPad device or a GOOGLE ANDROID based mobile phone or table, implementing a voice assistance program, application, or otherwise software including, for example, APPLE SIRI, GOOGLE ASSISTANT, MICROSOFT CORTANA, AMAZON ALEXA, or the like. More generally, assistant device 102v may comprise an electronic device including one or more microphones, one or more speakers, and/or one or more display screens for receiving input (e.g., audible input) and outputting data or information (e.g., via a speaker or displays screen).

In addition, voice assistant device 102v may implement or execute an operating system (OS) or mobile platform, such as APPLE's iOS, GOOGLE's ANDROID operating system, AMAZON's FIRE or ALEXA, MICROSOFT WINDOWS, operating systems, platforms, or the like. In various embodiments, voice assistant device 102v comprises one or more processors and/or one or more memories (e.g., a tangible, non-transitory computer-readable medium) for storing, implementing, or executing computing instructions or code, e.g., a voice assistant app, a home or personal assistant app, or otherwise, as described in various embodiments herein.

In the example of FIG. 1A, voice assistant device 102v may be an AMAZON ALEXA smart speaker device with one or more processor(s) and/or memorie(s) implementing a voice-assistant app executing, running, or otherwise implementing AMAZON ALEXA software.

The voice-assistant app of voice assistant device 102v comprises a voice command interface 112i configured to receive an audible input of a user. In the example of FIG. 1A, a voice command interface 112i may be implemented as an ALEXA Skill (software component) for receiving audible input at an ALEXA based voice assistance device (e.g., voice assistant device 102v). In various embodiments, audible input can include, for example, voice waves, signals, or audible sounds or information of a user for prompting voice assistant device 102v to receive or generate child event data (e.g., slot filling, name recognition, etc.), as described herein.

Figure 1B:
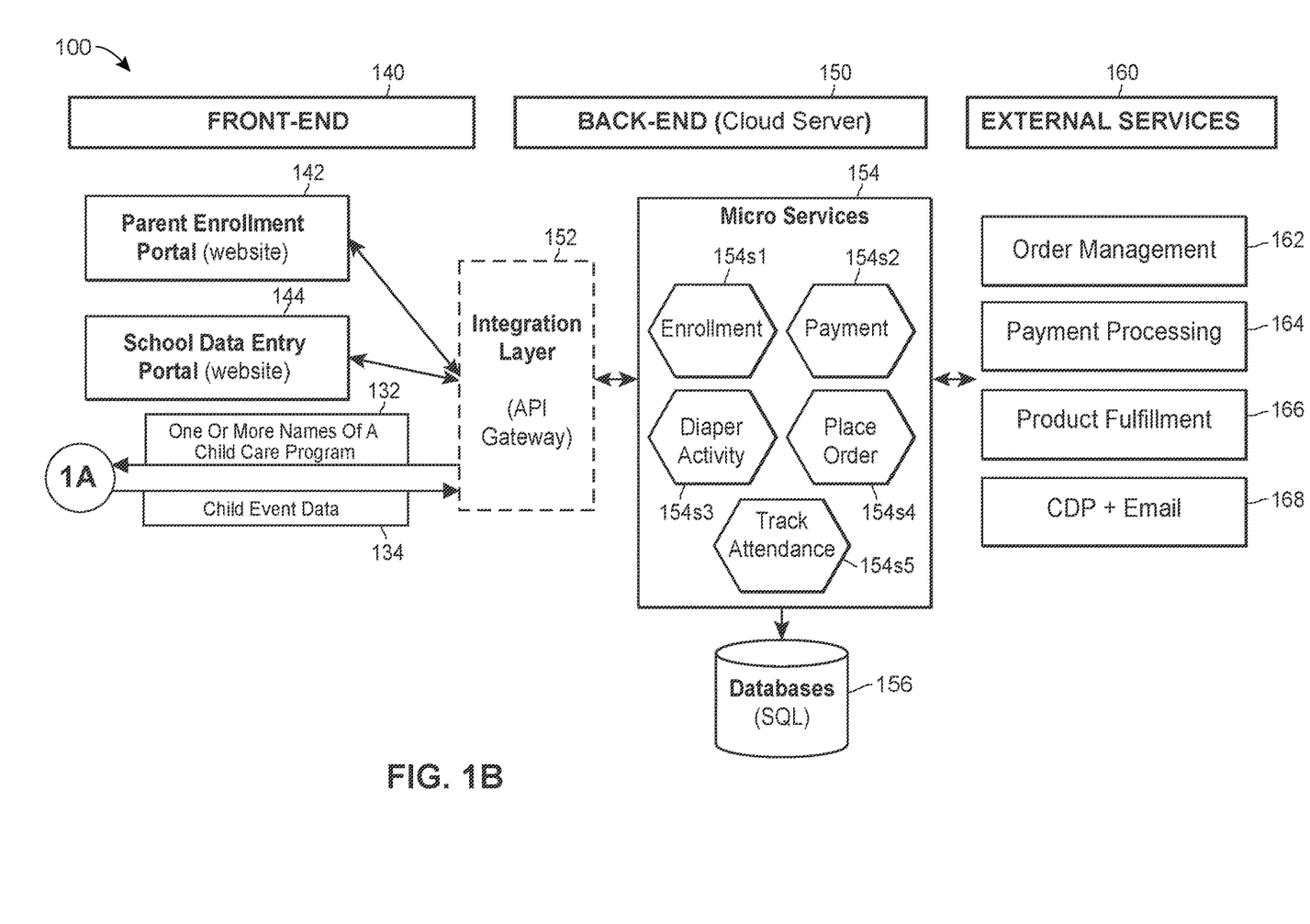
FIG. 1B further illustrates the example touch-free and voice-assistant system of FIG. 1A in accordance with various embodiments disclosed herein.

Voice-assistant app of voice assistant device 102v and/or voice command interface 112i are configured to send child event data 134 to one or more servers (e.g., server(s) 152 as described herein with respect to FIG. 1B). Child event data 134 is generated from, and is otherwise based on, the audible input of the user. Child event data 134 may comprise information related to use of one or more childcare products (e.g., diapers or other such child, personal, and/or hygienic related product). Child event data 134 is described further herein, for example, for FIGS. 2, 3, 4A and 4B.

In addition, in various embodiments, voice-assistant app of voice assistant device 102v and/or voice command interface 112i are configured to receive, from a server or cloud-based platform, one or more names 132 of a childcare program. For example, such information may comprise classroom child roster information and/or one or more children's full (or partial) names.

As illustrated for FIG. 1A, in some embodiments, voice-assistant app of voice assistant device 102v and/or voice command interface 112i may be configured to access a cloud-based platform 122, which may be used to process audible input, store information (e.g., child event data), and/or install or update related software (e.g., including voice-assistant app and/or voice command interface 112i). AMAZON WEB SERVICES (AWS) is an example cloud-based platform that may be accessed by voice-assistant app of voice assistant device 102v and/or voice command interface 112i. Other cloud-based platforms may be used as well, including MICROSOFT AZURE, GOOGLE CLOUD, or the like.

As illustrated for FIG. 1A, voice assistant device 102v and/or voice command interface 112i may access cloud-based platform 122 in order to call or access various cloud-based software components 122c1-122c6. Such components may be accessed via an application programming interface (API), such as a representational state transfer (RESTful) API over a computer network (e.g., the Internet). For example, a cloud manager cloud function 122c1 is a software component (for example, AWS Lambda), available via cloud-based platform 122, that is accessible by voice assistant device 102v and/or voice command interface 112i. Cloud function 122c1 is accessible for execution of remote application(s) or backend service(s), for processing audible input, storing information (e.g., child event data), and/or installing or updating related software (e.g., including voice-assistant app and/or voice command interface 112i) on the cloud-based platform 122.

Cloud function 122c1 can trigger or access other components, including, for example, cloud storage component 122c2 (e.g., which can be AWS S3 cloud storage), which is a software component, available via cloud-based platform 122, for storing data and reports (e.g., child event data). Cloud function 122c1 can trigger or access other components, including, for example, cloud API component 122c3 (e.g., which can be ALEXA FOR BUSINESS), security and identity component 124 (e.g., AMAZON CLOUD IAM) and source code repository component 122c5 (e.g., GITHUB source code repository) for managing developer roles and access, and for managing source code (e.g., of voice assistant device 102v and/or voice command interface 112i), respectively. Still further, cloud function 122c1 can trigger or access other components, including, for example, a logging and debugging component 122c6 (e.g., AMAZON CLOUDWATCH) for logging and debugging the operation or use of touch-free and voice-assistant system 100, including voice assistant device 102v and/or voice command interface 112i, or any one or more of components 122c1-122c6.

FIG. 1B further illustrates the example touch-free and voice-assistant system 100 of FIG. 1A in accordance with various embodiments disclosed herein. In the example of FIG. 1B, touch-free and voice-assistant system 100 includes one or more server(s) 152 comprising one or more processors and one or more memories. In some embodiments, server(s) 152 may comprise multiple servers, which may comprise a multiple, redundant, or replicated servers as part of a server farm. In still further embodiments, server(s) 152 may be implemented as cloud-based servers, such as a cloud-based computing platform. For example, server(s) 152 may be any one or more cloud-based platform(s) such as MICROSOFT AZURE, AMAZON AWS, or the like. For example, in the embodiment of FIG. 1B, server(s) 152 may be implemented as, at least a portion of, a back-end architecture 150 comprising MICROSOFT AZURE's cloud computing platform and/or services. Server(s) 152 may include one or more processor(s) as well as one or more computer memories.

The memories of server(s) 152 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memorie(s) may store an operating system (OS) (e.g., Microsoft Windows, Linux, UNIX, etc.) capable of facilitating the functionalities, apps, methods, or other software as discussed herein. The memories may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be configured to facilitate their various functionalities discussed herein. It should be appreciated that one or more other applications may be envisioned and that are executed by the processor(s) of server(s) 152. For example, one or more processor(s) of server(s) 152 may be connected to the memories via a computer bus responsible for transmitting electronic data, data packets, or otherwise electronic signals to and from the processor(s) and memories in order to implement or perform the machine readable instructions, methods, processes, elements or limitations, as illustrated, depicted, or described for the various flowcharts, illustrations, diagrams, figures, and/or other disclosure herein.

Server(s) 152 may further include a communication component configured to communicate (e.g., send and receive) data via one or more external/network port(s) to one or more networks or local terminals, such as a computer network as described herein. In some embodiments, server(s) 152 may include a client-server platform technology such as ASP.NET, Java J2EE, Ruby on Rails, Node.js, a web service or online API, responsive for receiving and responding to electronic requests. Server(s) 152 may implement the client-server platform technology that may interact, via the computer bus, with the memories(s) of server(s) 152 (including the applications(s), component(s), API(s), data, etc. stored therein) and/or database(s) 156 to implement or perform the machine readable instructions, methods, processes, elements or limitations, as illustrated, depicted, or described for the various flowcharts, illustrations, diagrams, figures, and/or other disclosure herein. According to some embodiments, server(s) 152 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to a computer network. In some embodiments, a computer network may comprise a private network or local area network (LAN). Additionally, or alternatively, a computer network may comprise a public network such as the Internet.

In general, a computer program or computer based product, application, or code may be stored on server(s) 152 via a memory, e.g., computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed or otherwise adapted to be executed by the processor(s) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

With reference to FIG. 1B, server 152 comprises an integration layer being exposed to outside computer requests. The integration layer may comprise an API gateway interface (e.g., which may be implemented as a RESTful API) for receiving requests via a computer network. Server 152, via its integration layer and/or API gateway interface, may receive and/or respond to requests, commands, or otherwise data or information of voice-assistant app of voice assistant device 102v and/or voice command interface 112i. For example, as shown in the example of FIG. 1B, server 152 may receive and/or send one or more names 132 of a childcare program and/or child event data 134 to and/or from of voice-assistant app of voice assistant device 102v and/or voice command interface 112i. In various embodiments, server 152 is communicatively coupled via a computer network (e.g., the Internet) to the voice-assistant app.

In the example of FIG. 1B, server(s) 152 is part of a back-end architecture 150. Back-end architecture 150 includes server 152, micro services 154, and database(s)

156. As shown in FIG. 1B, micro services 154 comprises various software components 154s1-154s5 that may be accessed by and/or that may return information or data to server(s) 152. For example, enrollment component 154s1 may include computing instructions and/or interface(s), executable and/or accessible by processor(s) of server(s) 152, for enrolling one or more name values (e.g., one or more names 132) corresponding to one or more children of a childcare program. Payment component 154s2 may include computing instructions and/or interface(s), executable and/or accessible by processor(s) of server(s) 152, for receiving payment details (e.g., credit card information, parent information, etc.) for purchasing inventory, childcare products, or otherwise handling purchases and/or transactions as described herein. Diaper activity component 154s3 may include computing instructions and/or interface(s), executable and/or accessible by processor(s) of server(s) 152, for tracking diaper related activity (e.g., recording specific child related event data, e.g., wet, dry, BM, and/or a number of diapers used, etc.), as described herein. Order placement component 154s4 may include computing instructions and/or interface(s), executable and/or accessible by processor(s) of server(s) 152, for placing orders to maintain and/or track inventory, childcare products, or otherwise managing inventory as described herein. Attendance tracking component 154s5 may include computing instructions and/or interface(s), executable and/or accessible by processor(s) of server(s) 152, for tracking attendance (e.g., daily, weekly, etc.) of children of the childcare program or otherwise roster, which may include tracking one or more name values (e.g., one or more names 132) corresponding to one or more children of a childcare program.

In various embodiments, one or more of software components 154s1 to 154s5 may access or store information in database(s) 156. Database(s) 156 may include or comprise databases (e.g., relational database(s), such as Oracle, DB2, MySQL, or a NoSQL based database, such as MongoDB). Database(s) 156 may use SQL for receiving, providing, and/or storing data and/or information (e.g., such as one or more names 132 of a childcare program and/or child event data 134 as described herein).

In the example of FIG. 1B, server(s) 152, back-end architecture 150 may receive requests from, and/or may provide data to, front end architecture 140. Front-end architecture 140 may include various web sites and/or web pages (e.g., distributed and/or hosted by server(s) 152) via hypertext markup language (HTML), which may, in turn, provide computing instructions for accessing and/or providing information to server(s) 152. For example, parent enrollment portal website 142 may comprise one or more webpages that may access enrollment component 154s1 for enrolling one or more children into a childcare program. School data entry portal website 144 may comprise one or more webpages used by a teacher or other administrator of the childcare program, e.g., for tracking attendance (e.g., via attendance tracking component 154s5) or tracking or managing diaper activity and/or inventory (e.g., via diaper activity component 154s3 via voice-assistant app of voice assistant device 102v and/or voice command interface 112i). Front-end architecture 140 may also include one or more mobile applications (app), as implemented natively via APPLE iOS or GOOGLE ANDROID, that can access server(s) 152 of back-end architecture 150, similar to websites 142 and 144.

In various embodiments, back-end architecture 150 may access, provide information to, and/or receive information from external services 160, including software services 162-168 as provided by third-parties, which may comprise API based services accessible by server(s) 152 and/or micro services 154 (including any of software components 154s1-154cs), either directly and/or via a computer network (e.g., the Internet). For example, external services 160 may include order management service 162 (e.g., as provided by the BIG COMMERCE order management platform) for managing orders (e.g., as received from, or access via, order placement component 154s4). As another example, external services 160 may include payment processing service 164 (e.g., as provided by the CYBERSOURCE platform) for payment processing (e.g., as received from, or access via, order payment component 154s2). As another example, external services 160 may include product fulfillment service 166 (e.g., as provided by the AREO platform) for product fulfillment (e.g., as received from, or access via, order payment component 154s4). As a still further example, external services 160 may include a customer data platform (CDP) and email service 168 (e.g., as provided by the SEGMENT platform) for providing a customer data platform (CDP), and for communications to and from parents regarding attendance tracking (e.g., as received from, or access via, attendance tracking component 154s5).

Figure 2:
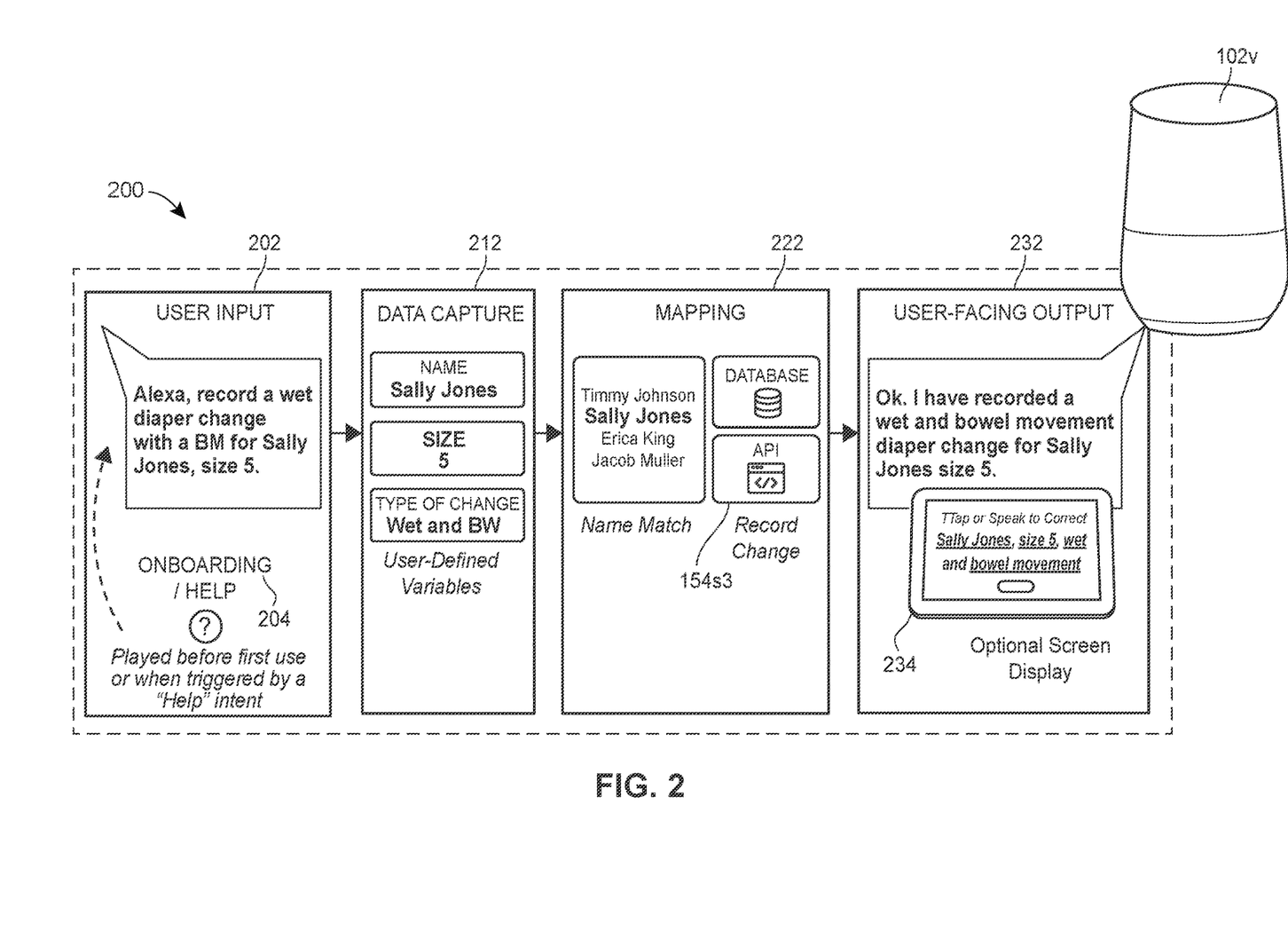
FIG. 2 illustrates a flow diagram of an example touch-free and voice-assistant method in accordance with various embodiments disclosed herein.

FIG. 2 illustrates a flow diagram of an example touch-free and voice-assistant method 200 in accordance with various embodiments disclosed herein. At block 202, method 200 comprises receiving, by one or more processors, one or more name values (e.g., one or more names 132) corresponding to one or more children of a childcare program associated with at least one physical childcare location. The one or more name values may be determined based on audible input of a user. In the example of FIG. 2, a user provides audible input by speaking a verbal command: "Alexa, record a wet diaper change with a BM for Sally Jones, size 5." Such audible input may be received by voice assistance app executing on one or more processors of voice assistant device 102v. In turn, such information may be sent to one or more processors of server(s) 152, e.g., which may comprise of child event data, as described herein. In this way, audible input of a user may be used to create a fixed universe of names (e.g., one or more names 132) of children in a program (e.g., a childcare program, such as a daycare program).

In some embodiments, as shown in FIG. 2, at 204, voice assistance app may also receive audible input from the user for "help," which may trigger an audible menu or greeting that instructs the user which commands are available for interaction with voice assistant device 102v. Such audible menu or greeting may also be played or provided upon a first use of voice assistant device 102v and/or voice assistant app.

In various embodiments, the one or more names 132 may represent a classroom or child roster of one or more children of a childcare program. The one or more names 132 may comprise full name(s) of a child and/or may comprise user IDs (of a child and/or the child's parent). Still further, in some embodiments, each of the one or more names 132 may comprise unique values (e.g., unique names and/or user IDs).

Method 200 may further comprise generating, by the one or more processors (e.g., processors of server(s) 152), a childcare product inventory based on a count of the one or more name values (e.g., one or more names 132). The childcare product inventory may be an inventory for a childcare program (e.g., inventory at a school level). In various embodiments, the childcare product inventory may comprise a childcare product of at least one product type. For example, in the embodiment of FIG. 2, the childcare product is a diaper.

Method 200 may further comprise receiving, by the one or more processors (e.g., servers(s) 152), child event data comprising information related to use of the childcare product (e.g., a diaper). Such child event data may be based on audible input of a user as received via a voice command interface (e.g., voice command interface 112*i*) of a voice-assistant application (app) as implemented on a voice assistance device (e.g., voice assistant device 102*v*), for example, as described for FIGS. 1A and 1B herein.

In various embodiments, child event data may comprise one or more of: a name value (e.g., a name of a child) of the one or more name values (e.g., names 132), a type of event value, an event date, an event time, or a size of the childcare product. Still further, child event data may comprise a change event (e.g., a diaper change event) corresponding to a child of the one or more children. For example, at block 212, method 200 comprises data capture of a child event data comprising a name ("Sally Jones"), size of childcare product (e.g., size 5 of a diaper), and type of event value (e.g., "wet and BM"). In some embodiments, the values may be user-defined and/or product specific. For example, for a diaper product, valid type of event values may comprise: BM (bowel movement), wet, dry, and/or mixed.

At block 222, method 200 may further comprise mapping and/or storing child event data. For example, the child event data captured in block 212 may be sent to server(s) 152 for processing by diaper activity component 154*s*3 for mapping and/or storage (e.g., in database(s) 156). For example, as illustrated in FIG. 2, child event data may be used (e.g., by server(s) 152) to lookup or otherwise use the name of the child event data to identify or match the child, as compared to other children participating or enrolled in a childcare program. Additionally, or alternatively, the child's related user ID may be used. Such child event data may be looked-up, mapped, and/or stored in database(s) 156 via name matching the child's name and/or user ID from a list, table, or otherwise data structure of database(s) 156.

Method 200 may further comprise reporting, processing, and/or storage of child event data. For example, at block 232 server(s) 152 may comprise computing instructions, that when executed by one or more processors of server(s) 152, may cause the one or more processors of the server to provide an audible output to the voice-assistant app. For example, such audible output may be provided, e.g., via a computer network (e.g., the Internet), to the voice-assistant app of voice assistant device 102*v*. The audible output may cause the voice assistant device 102*v* to announce or indicate (e.g., either audibly or visually) a confirmation that the child event data has been recorded. For example, as shown in the example of FIG. 2, at block 232, server(s) 152 may transmit, to voice-assistant app of voice assistant device 102*v*, audible output indicating that child event data (as described for blocks 202, 212, and 222) have been recorded. For example, in one embodiment, the audible output may be a statement played by voice assistant device 102*v*, e.g., "Ok. I have recorded a wet and bowel movement diaper change for Sally Jones size 5."

In some embodiments, a display screen 234 may also be configured, e.g., with voice assistant device 102*v*, to provide visual output. For example, in some embodiments, data or information of one or more of the audible input of a user, the one or more name values, the child event data, or the childcare product inventory may be provided to and displayed on display screen 234. Display screen 234 may be communicatively coupled to at least one of the voice-assistant app of voice assistant device 102*v* and/or server(s) 152. In the example of FIG. 2, the audible input of the user is (from block 202) is displayed on display screen 234.

Method 200 may further comprise updating, by the one or more processors (e.g., one or more processors of server(s) 152), the childcare product inventory based on the child event data. In various embodiments, an amount or count of childcare product(s) may be recorded, increased, or otherwise tracked based on the child event data. For example, receipt of the child event data may cause server(s) 152 to decrement the count. In addition, receipt of order related information (e.g., via order placement component 154*s*4) may cause server(s) 152 to increment count. For example, in the embodiment of FIG. 2, a change event (regarding using a diaper of size 5) may cause the inventory count to be decreased by a count of one. This may cause server(s) 152, via order placement component 154*s*4, to place an order for more diapers (e.g., of size 5) to automatically manage the inventory of the child/daycare program.

In various embodiments, server(s) 152 may also track inventory at the daycare level (across all children) or at the specific child level (on a per child basis). For example, receipt of the child event data may cause a child-specific tracked inventory of a given child to be updated. In this way, the number of childcare products as used by a given child may be tracked (e.g., via credits/debits) of an inventory specific to a given a child.

Figure 3:
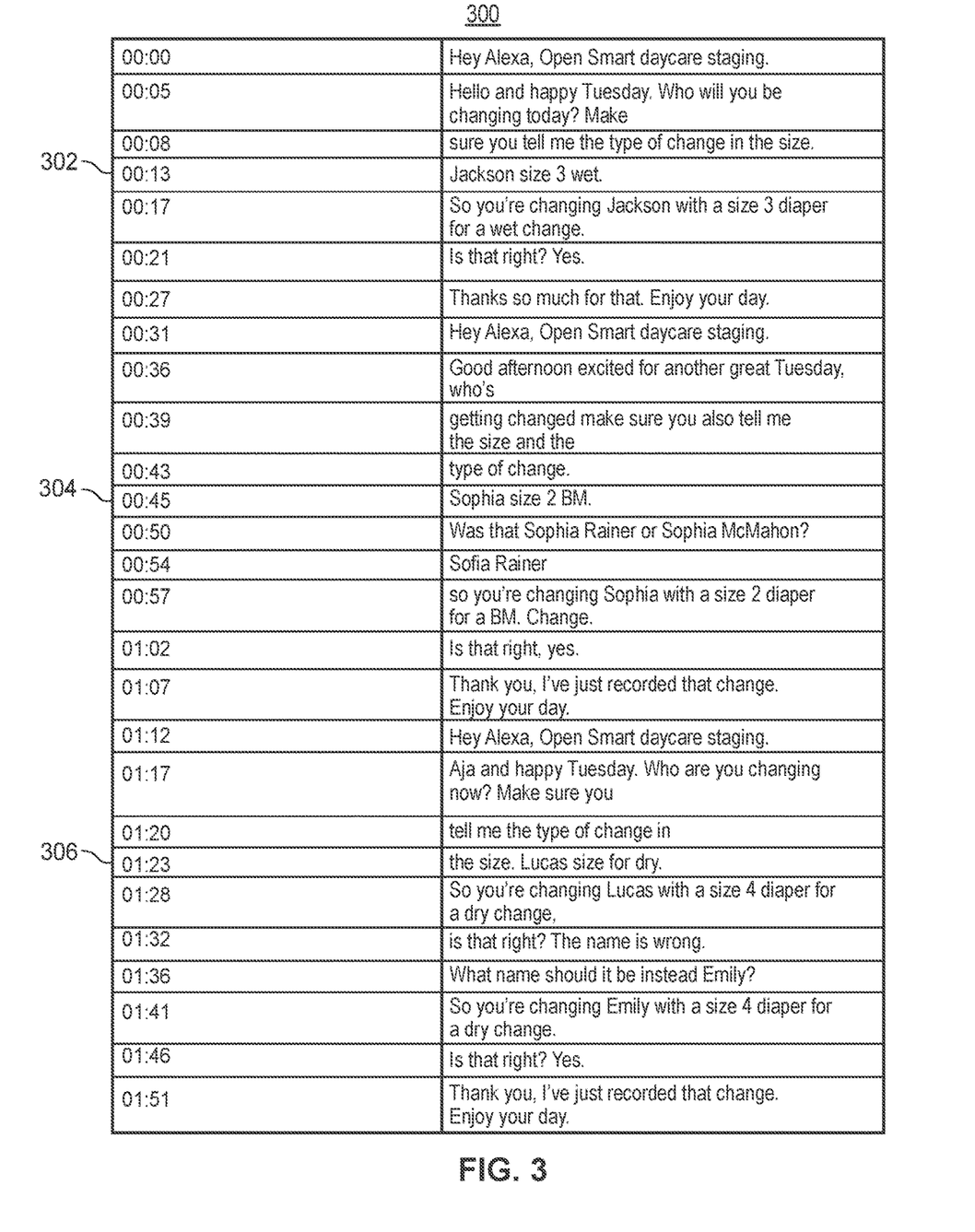
FIG. 3 illustrates an example transcript comprising audible input of a user as provided to a voice-assistant app in accordance with various embodiments disclosed herein.

FIG. 3 illustrates an example transcript comprising audible input of a user as provided to a voice-assistant app of a voice assistant device (e.g., voice assistant device 102*v*), in accordance with various embodiments disclosed herein. FIG. 3 comprises audible input of a user as to three different children. For example, for portion 302 (beginning at time 00:13), audible input includes input comprising child event data specifying a name ("Jackson") of child that is being changed having a wet diaper of size 3. Portion 302 is similar the example of FIG. 2, such that voice-assistant system 100 would operate as described for FIG. 2.

For portion 304 (beginning at time 00:45), however, audible input includes input comprising ambiguous child event data specifying a name ("Sofia") of a child is being changed having a BM diaper of size 2. The name "Sofia" is ambiguous because two children are named Sofia. In such embodiments, server(s) 152 comprise computing instructions, that when executed by the one or more processors of server(s) 152, cause the one or more processors of the server to send a request (portion 304, at time 00:50) to confirm a name value of the one or more name values to the voice-assistant app of voice assistant device 102*v*. Server(s) 152 may receive a response corresponding to the name value corresponding to an additional audible input of the user, e.g., confirming a correct name (e.g., "Sofia Reiner," portion 304, at time 00:54) and/or other child event data (e.g., confirming changing Sofia Reiner at with a size 2 diaper for a BM change (portion 304, at time 00:57 and 01:02)).

As a further example, voice-assistant system 100 comprises the ability to receive unrecognizable child event data, comprising a child's name, and then propose back to the user some possible options to be confirmed. For example, for portion 306 (beginning at time 01:23), audible input is provided by the user that includes a name value, where the name value corresponds to a name not in database(s) 156. That is, the child event data based on the user's audible input comprises an unrecognizable name value that does not correspond to the one or more children of the childcare program. In such embodiments, server(s) 152 may access database(s) 156 to identify a suggested name, and then suggest, via provision to the voice assistant app of voice assistant device 102v, the suggested name value to the user. For example, as shown in the FIG. 3, for portion 306 (beginning at time 01:23), the user states "Lucas size . . . dry." However, "Lucas," is not in database(s) 156. Server(s) 152 may scan database(s) 156 to locate, and then propose, that a suggested name (e.g., portion 306 (at time 01:36) and, as shown, a specific related size. Server(s) 152 and/or voice assistance app of voice assistant device 102v may then confirm the correct name and/or other child event data (e.g., portion 306 (at times 01:41 and 01:46)).

Figure 4A:
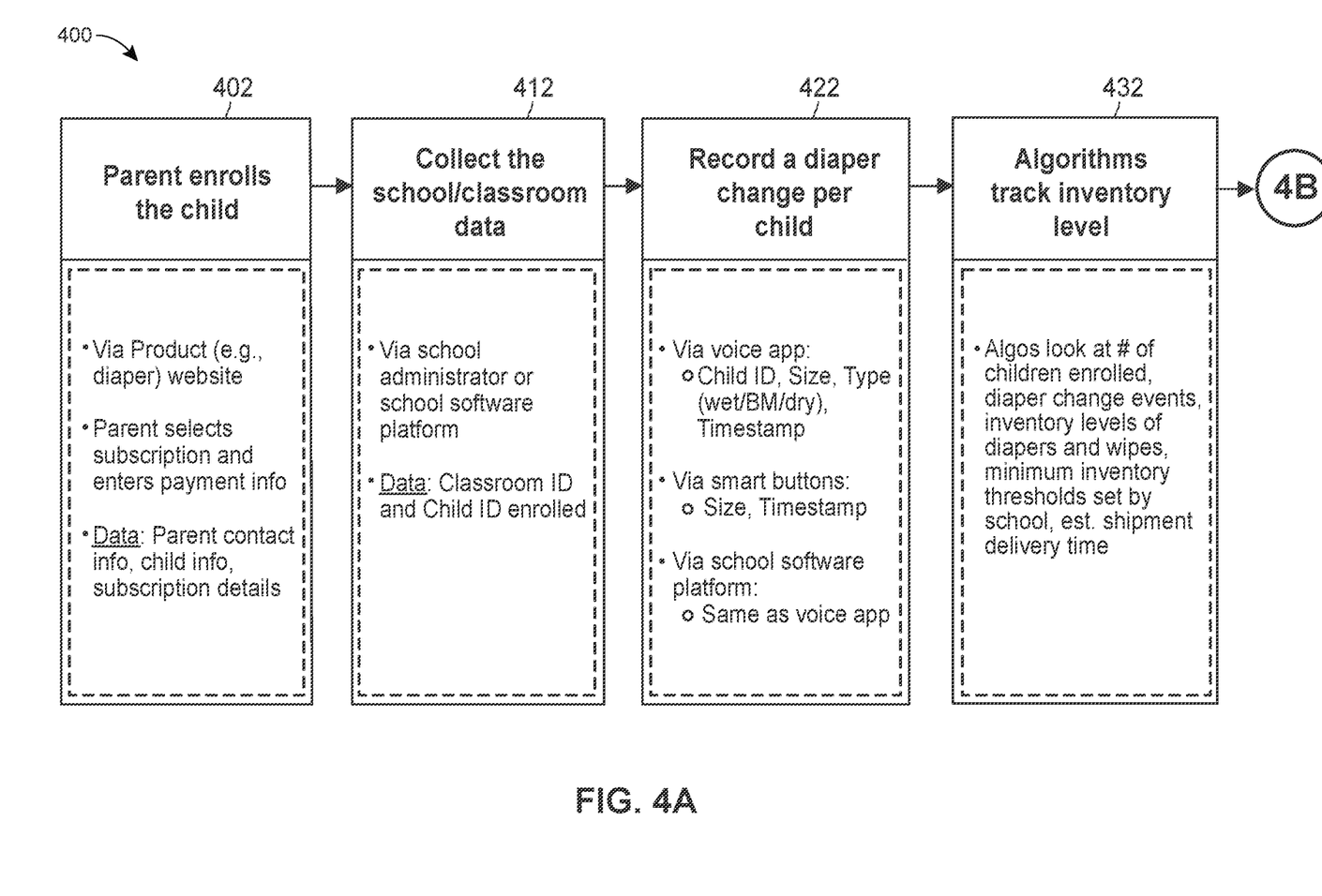
FIG. 4A illustrates a flow diagram of a further example touch-free and voice-assistant method in accordance with various embodiments disclosed herein.

FIG. 4A illustrates a flow diagram of a further example touch-free and voice-assistant method 400 in accordance with various embodiments disclosed herein. Generally, FIG. 4A, together with FIG. 4B (as described herein below), illustrate an end-to-end (E2E) process involving or using touch-free and voice-assistant systems and methods as described herein (e.g., touch-free and voice-assistant system 100 and/or touch-free and voice-assistant method 200).

With reference to FIG. 4A, at block 402, a parent may enroll a child in a childcare program. Such enrollment may involve selecting childcare products required or used by the childcare program and/or submitting child name(s) and/or other information as described herein. For example, in various embodiments, server(s) 152 may comprise computing instructions, that when executed by the one or more processors, cause the one or more processors of server(s) 152 to render an enrollment graphical user interface (GUI) (e.g., parent enrollment portal website 142) configured for display on a display screen of a user interface device. For example, a user interface device can comprise a personal computer that executes a web browser or a mobile device that implements a native app. In such embodiments, one or more name values (e.g., one or more names 132) corresponding to one or more children may be received from the enrollment GUI. As a further example, and as illustrated by block 402, such enrollment can involve a parent or guardian visiting an enrollment website (e.g., parent enrollment portal website 142) for selecting subscription settings (e.g., payment plan or information, e.g., $2 per day via a credit card) for a childcare product (e.g., diapers), and entering other data related to the childcare program, such as parent contact info, child info (e.g., a child name, postal address of child, desired teacher, etc. for storage by database(s) 156 as described herein), and other subscription details. Enrollment (e.g., via parent enrollment portal website 142) may cause the related enrollment information to be received by server(s) 152. Such enrollment, payment, and product ordering may be implemented or otherwise handled by enrollment component 154s1, payment component 154s2, order placement component 154s4, or via other software, components (e.g., any one or more of components 154s1-154s5), and/or services (e.g., services 162-168) as described herein.

As illustrated by FIG. 4A, at block 412, server(s) 152 may receive and/or collect school and/or classroom data as provided, for example, by a parent and/or other user as described for block 402. Such data may include classroom ID, a user ID, child ID, one or more children names, etc. as described herein. Such data may be collected, arranged, organized by a school administrator and/or software platform (e.g., back-end architecture 150) as described herein.

As illustrated by FIG. 4A, at block 422, server(s) 152 may receive data, such as child event data, as provided, for example, by voice assistant app and/or voice command interface 112i of assistant device 102v as described herein. Data collected may include child ID, size, product type information (e.g., wet, BM, dry, etc. for a diaper change), a timestamp, and other such data as described herein. Such data may be collected, arranged, organized by a software platform (e.g., back-end architecture 150) as described herein.

Additionally or alternatively, a "smart button" may be used to collect child event data in conjunction with, or as an alternative to, collection of such data via a voice app. A smart button may comprise a wired or wireless electronic device, that provides input via a user's selection or push of the smart button. In various embodiments, a smart button may wirelessly communicate (e.g., via the BLUETOOTH standard) with a receiver. The receiver may send signals and/or data to server(s) 152 as described herein for assistant device 102v. A smart button may implement APPLE iOS, GOOGLE ANDROID, or other operating system software, platforms to allow for the use of respective native apps. An example smart button is a FLIC smart button, which comprises a small, wireless push button that can control apps, devices, and/or services. The FLIC smart button operates via a physical button rather than using different apps or voice commands. A FLIC smart button may be used to control devices and services, and may be used to communicate data with server(s) 152. For example, a FLIC smart button (or other such smart button) may be programmed or otherwise configured to send child event data and/or other data to server(s) 152. For example, a smart button (e.g., FLIC smart button) may be configured to send different child event data (e.g., different sizes, types (e.g., wet, dry, BM, etc.) based on different push or interaction types (e.g., push, double push, hold, etc.). Data collected via a smart button may include child ID, size, product type information (e.g., wet, BM, dry, etc. for a diaper change), a timestamp, and other such data as described herein. Such data may be collected, arranged, organized by a software platform (e.g., back-end architecture 150) as described herein.

As illustrated by FIG. 4A, at block 432, server(s) 152, and related software components (e.g., any one or more of 154s1-154s5) may analyze data, including one or more names 132 and/or child event data 134 as described herein, for the purposes of tracking child products, managing inventory, placing orders, etc. For example, server(s) 152 may analyze children enrolled in a childcare program (e.g., via analyzing one or more names 132), diaper change events (e.g., via diaper activity component 154s3), inventory levels of childcare products (e.g., diapers and wipes), minimum inventory thresholds, shipment delivery times, etc. as described herein.

Figure 4B:
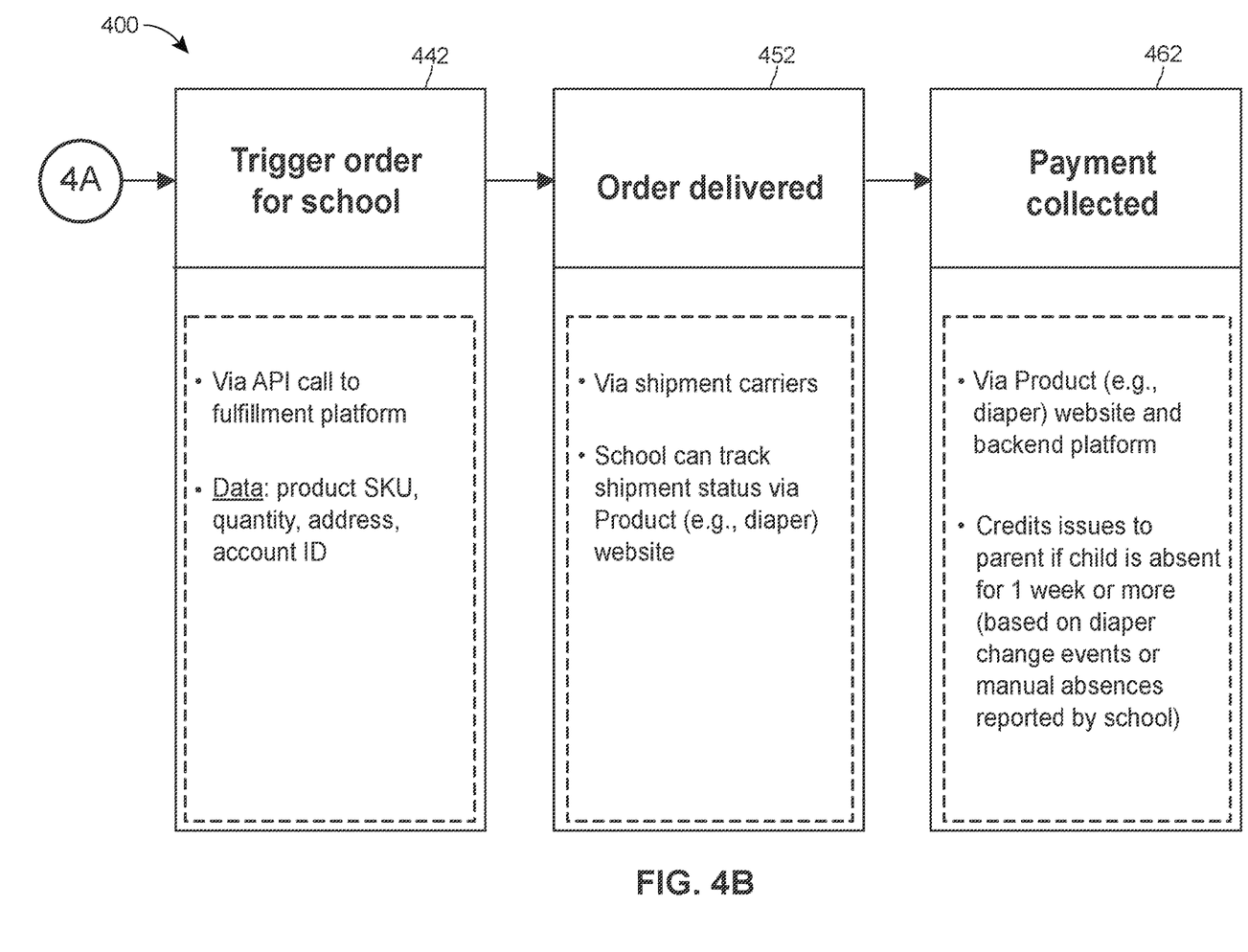
FIG. 4B further illustrates the example touch-free and voice-assistant method of FIG. 4A in accordance with various embodiments disclosed herein.

FIG. 4B further illustrates the example touch-free and voice-assistant method 400 of FIG. 4A in accordance with various embodiments disclosed herein. As illustrated for block 442, server(s) 152 may comprise computing instructions, that when executed by one or more processors of server(s) 152, cause the one or more processors of the server to initiate an order for provision of one or more additional childcare products of the at least one product type (e.g., diapers or wipes) to a physical childcare location of a given childcare program. Such functionally provides a flow of communications between voice-assistant system 100 and a provider of childcare products. For example, server(s) 152 may utilize order payment component 154s4 and/or Big Commerce service 162, via API calls, to initiate order fulfillment. Information provided for order fulfillment may include product SKU, quantity of products, address of the physical location (e.g., of the childcare program), account ID, and/or other data as described herein.

As illustrated for block 452, server(s) 152 order fulfillment, as described for block 442, may comprise shipment of childcare products via various carriers (FedEx, UPS, etc.).

Order fulfillment may also comprise server(s) 152 tracking shipment status via a tracking id, website, or otherwise for users, teachers, administrators, or software (e.g., back-end platform 150) to track and/or manage childcare product inventory. For example, server(s) 152, may track orders via inventory levels (e.g., via product SKU, etc.), a tracking id, and/or increments/decrements of use of childcare products, as described herein, in order to automatically replenish inventory on an as-need basis.

As illustrated for block 462, payment fulfillment or collection for orders as described for blocks 442 and/or 452, may be performed by back-end platform 150. For example, server(s) 152 may issue or otherwise manage payment via payment component 154$s$2 and/or CyberSource service 164. Additionally, or alternatively, server(s) 152 may issue credits to user (e.g., parents) based on a child's participation in a childcare program. For example, if a child is absent for a week or more, then credits/debits of childcare products (and related payments therefor) may be attributed to the child (or its related account). Such credits/debits may be based on diaper change events or absences as reported and/or tracked by back-end platform 150 (e.g., via attendance tracking component 154$s$5).

Aspects of the Present Disclosure

The following aspects of the disclosure are exemplary only and not intended to limit the scope of the disclosure.

1. A touch-free, voice-assistant, and/or tracking system configured to automate inventory generation and tracking of childcare products, the touch-free, voice-assistant, and/or tracking system comprising: a voice-assistant application (app) comprising computing instructions configured for implementation on a voice assistant device, the voice-assistant app comprising a voice command interface configured to receive an audible input of a user; and a server comprising one or more processors and one or more memories, and the server communicatively coupled via a computer network to the voice-assistant app, wherein the server comprises computing instructions configured to execute on the one or more processors of the server, wherein the computing instructions, when executed by the one or more processors, cause the one or more processors of the server to: receive one or more name values corresponding to one or more children of a childcare program associated with at least one physical childcare location, generate a childcare product inventory based on a count of the one or more name values, the childcare product inventory comprising a childcare product of at least one product type, receive child event data, from the voice-assistant app, comprising information related to use of the childcare product, wherein the child event data is based on the audible input of the user, and update the childcare product inventory based on the child event data.

2. The touch-free, voice-assistant, and/or tracking system of aspect 1, wherein the child event data comprises a change event corresponding to a child of the one or more children.

3. The touch-free, voice-assistant, and/or tracking system of aspect 2, wherein the childcare product is a diaper.

4. The touch-free, voice-assistant, and/or tracking system of aspect 2, wherein receipt of the child event data causes a child-specific tracked inventory of the child to be updated.

5. The touch-free, voice-assistant, and/or tracking system as in any one of aspects 1-4, wherein the child event data comprises one or more of: a name value of the one or more name values, a type of event value, an event date, an event time, or a size of the childcare product.

6. The touch-free, voice-assistant, and/or tracking system as in any one of aspects 1-5, wherein each of the one or more name values are unique values.

7. The touch-free, voice-assistant, and/or tracking system as in any one of aspects 1-6, wherein the computing instructions, when executed by the one or more processors, further cause the one or more processors of the server to: initiate an order for provision of one or more additional childcare products of the at least one product type to the physical childcare location.

8. The touch-free, voice-assistant, and/or tracking system as in any one of aspects 1-7, wherein the computing instructions, when executed by the one or more processors, further cause the one or more processors of the server to: provide an audible output to the voice-assistant app, the audible output configured to cause the voice assistant device announce or indicate a confirmation that the child event data has been recorded.

9. The touch-free, voice-assistant, and/or tracking system as in any one of aspects 1-8, wherein the computing instructions, when executed by the one or more processors, further cause the one or more processors of the server to: send a request to confirm a name value of the one or more name values to the voice-assistant app, and receive a response corresponding to the name value, the response corresponding to an additional audible input of the user.

10. The touch-free, voice-assistant, and/or tracking system of aspect 9, wherein the name value is a suggested name value, and wherein the child event data comprises an unrecognizable name value that does not correspond to the one or more children of the childcare program.

11. The touch-free, voice-assistant, and/or tracking system as in any one of aspects 1-10, wherein the computing instructions, when executed by the one or more processors, further cause the one or more processors of the server to: render an enrollment graphical user interface (GUI) configured for display on a display screen of a user interface device, wherein the one or more name values corresponding to one or more children are received from the enrollment GUI.

12. The touch-free, voice-assistant, and/or tracking system as in any one of aspects 1-11, wherein data or information of one or more of the audible input of a user, the one or more name values, the child event data, or the childcare product inventory is provided to and displayed on a display screen communicatively coupled to at least one of the voice-assistant app or the server.

13. A touch-free, voice-assistant, and/or tracking method for automating inventory generation and tracking of childcare products, the touch-free, voice-assistant, and/or tracking method comprising: receiving, by one or more processors, one or more name values corresponding to one or more children of a childcare program associated with at least one physical childcare location; generating, by the one or more processors, a childcare product inventory based on a count of the one or more name values, the childcare product inventory comprising a childcare product of at least one product type; receiving, by the one or more processors, child event data comprising information related to use of the childcare product, wherein the child event data is based on audible input of a user, the audible input received via a voice command interface of a voice-assistant application (app) as implemented on a voice assistance device; and updating, by the one or more processors, the childcare product inventory based on the child event data.

14. A tangible, non-transitory computer-readable medium storing instructions for automating inventory generation and tracking of childcare products, that when executed by one or more processors cause the one or more processors to: receive one or more name values corresponding to one or more children of a childcare program associated with at least one physical childcare location; generate a childcare product inventory based on a count of the one or more name values, the childcare product inventory comprising a childcare product of at least one product type; receive child event data comprising information related to use of the childcare product, wherein the child event data is based on audible input of a user, the audible input received via a voice command interface of a voice-assistant application (app) as implemented on a voice assistance device; and update the childcare product inventory based on the child event data.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A voice-assistant system configured to automate inventory generation and tracking of childcare products, the voice-assistant system comprising:
    a voice-assistant application (app) comprising computing instructions configured for implementation on a voice assistant device, the voice-assistant app comprising a voice command interface configured to receive an audible input of a user; and
    a server comprising one or more processors and one or more memories, and the server communicatively coupled via a computer network to the voice-assistant app, wherein the server comprises computing instructions configured to execute on the one or more processors of the server, wherein the computing instructions, when executed by the one or more processors, cause the one or more processors of the server to:
    receive one or more name values corresponding to one or more children of a childcare program associated with at least one physical childcare location, generate a childcare product inventory based on a count of the one or more name values, the childcare product inventory comprising a childcare product of at least one product type,
    receive an audible input of the user, implement data capture wherein the voice-assistant app processes the audible input of the user to detect user-defined variables of child event data comprising at least one user-defined variable identifying the childcare product as audibly detected within the audible input,
    wherein the one or more name values, the child event data, or the childcare product inventory is provided to and displayed on a display screen communicatively coupled to at least one of the voice-assistant app or the server; and
    in response to the audible input of the user, displaying the one or more name values, the child event data, or the childcare product inventory on a display screen communicatively coupled to at least one of the voice-assistant app or the server and
    providing an audible output to the voice-assistant app, the audible output configured to cause the voice assistant device to announce or indicate a confirmation that the child event data has been recorded;
    and update the childcare product inventory based on the child event data.

2. The voice-assistant system of claim 1, wherein the child event data comprises a change event corresponding to a child of the one or more children.

3. The voice-assistant system of claim 2, wherein the childcare product is a diaper.

4. The voice-assistant system of claim 2, wherein receipt of the child event data causes a child-specific tracked inventory of the child to be updated.

5. The voice-assistant system of claim 1, wherein the child event data comprises one or more of: a name value of the one or more name values, a type of event value, an event date, an event time, or a size of the childcare product.

6. The voice-assistant system of claim 1, wherein each of the one or more name values are unique values.

7. The voice-assistant system of claim 1, wherein the computing instructions, when executed by the one or more processors, further cause the one or more processors of the server to: initiate an order for provision of one or more additional childcare products of the at least one product type to the physical childcare location.

8. The voice-assistant system of claim 1, wherein the computing instructions, when executed by the one or more processors, further cause the one or more processors of the server to: send a request to confirm a name value of the one or more name values to the voice-assistant app, and receive a response corresponding to the name value, the response corresponding to an additional audible input of the user.

9. The voice-assistant system of claim 8, wherein the name value is a suggested name value, and wherein the child event data comprises an unrecognizable name value that does not correspond to the one or more children of the childcare program.

10. The voice-assistant system of claim 1, wherein the computing instructions, when executed by the one or more processors, further cause the one or more processors of the server to: render an enrollment graphical user interface (GUI) configured for display on a display screen of a user interface device, wherein the one or more name values corresponding to one or more children are received from the enrollment GUI.

11. A voice-assistant method for automating inventory generation and tracking of childcare products, the voice-assistant method comprising:

receiving, by one or more processors, one or more name values corresponding to one or more children of a childcare program associated with at least one physical childcare location;

generating, by the one or more processors, a childcare product inventory based on a count of the one or more name values, the childcare product inventory comprising a childcare product of at least one product type;

receiving, by the one or more processors, an audible input of the of a user implementing, by the one or more processors, data capture wherein a voice-assistant application (app) processes the audible input of the user to detect user-defined variables of child event data comprising at least one user-defined variable identifying the childcare product as audibly detected within the audible input the audible input received via a voice command interface of the voice-assistant as implemented on a voice assistance device; and wherein the one or more name values, the child event data, or the childcare product inventory is provided to and displayed on a display screen communicatively coupled to at least one of the voice-assistant app or a server; and in response to the audible input of the user, displaying the one or more name values, the child event data, or the childcare product inventory on a display screen communicatively coupled to at least one of the voice-assistant app or the server and providing an audible output to the voice-assistant app, the audible output configured to cause the voice assistant device to announce or indicate a confirmation that the child event data has been recorded;

updating, by the one or more processors, the childcare product inventory based on the child event data.

12. The voice-assistant method of claim 11, wherein the child event data comprises a change event corresponding to a child of the one or more children.

13. The voice-assistant method of claim 12, wherein the childcare product is a diaper.

14. The voice-assistant method of claim 12, wherein receipt of the child event data causes a child-specific tracked inventory of the child to be updated.

15. The voice-assistant method of claim 11, wherein the child event data comprises one or more of: a name value of the one or more name values, a type of event value, an event date, an event time, or a size of the childcare product.

16. The voice-assistant method of claim 12, wherein each of the one or more name values are unique values.

17. The voice-assistant method of claim 12 further comprising: initiating an order for provision of one or more additional childcare products of the at least one product type to the physical childcare location.

18. The voice-assistant method of claim 12 further comprising: sending a request to confirm a name value of the one or more name values to the voice-assistant app, and receiving a response corresponding to the name value, the response corresponding to an additional audible input of the user.

19. The voice-assistant method of claim 18, wherein the name value is a suggested name value, and wherein the child event data comprises an unrecognizable name value that does not correspond to the one or more children of the childcare program.

20. The voice-assistant method of claim 11 further comprising: rendering an enrollment graphical user interface (GUI) configured for display on a display screen of a user interface device, wherein the one or more name values corresponding to one or more children are received from the enrollment GUI.

21. A tangible, non-transitory computer-readable medium storing instructions for automating inventory generation and tracking of childcare products, that when executed by one or more processors cause the one or more processors to:

receive one or more name values corresponding to one or more children of a childcare program associated with at least one physical childcare location;

generate a childcare product inventory based on a count of the one or more name values, the childcare product inventory comprising a childcare product of at least one product type;

receive an audible input of the of a user;

implement data capture wherein a voice-assistant application (app) processes the audible input of the user to detect user-defined variables of child event data comprising at least one user-defined variable identifying the childcare product as audibly detected within the audible input child event data comprising information related to use of the childcare product, wherein the child event data is based on audible input of a user, the audible input received via a voice command interface of the voice-assistant application (app) as implemented on a voice assistance device;

wherein the one or more name values, the child event data, or the childcare product inventory is provided to and displayed on a display screen communicatively coupled to at least one of the voice-assistant app or a server; and in response to the audible input of the user, displaying the one or more name values, the child event data, or the childcare product inventory on a display screen communicatively coupled to at least one of the voice-assistant app or the server and providing an audible output to the voice-assistant app, the audible output configured to cause the voice assistant device to announce or indicate a confirmation that the child event data has been recorded;

and update the childcare product inventory based on the child event data.

* * * * *